(12) United States Patent
Hahn et al.

(10) Patent No.: US 6,399,827 B1
(45) Date of Patent: *Jun. 4, 2002

(54) QUATERNARY AMMONIUM PHOSPHATE COMPOUND AND METHOD OF PREPARING SAME

(75) Inventors: Soon-Jong Hahn, Seoul; Jeong-Joo Shin; Jae-Min Ha, both of Suwon-si; Chang-Mook Cho, Seoul; Ki-Man Park, Suwon-si; Kwang-Hee Yoo, Uiwang-si; Dong-Jin Choi, Anyang-si; Jun-Weon Park, Seongnam-si, all of (KR)

(73) Assignee: SK Chemicals, Kyungki-do ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/508,382
(22) PCT Filed: Apr. 24, 1998
(86) PCT No.: PCT/KR98/00099
§ 371 Date: Jun. 12, 2000
(87) PCT Pub. No.: WO99/12889
PCT Pub. Date: Mar. 18, 1999

(30) Foreign Application Priority Data

Sep. 10, 1997 (KR) .............................. 97-46517

(51) Int. Cl.⁷ ........................................... C07C 211/62
(52) U.S. Cl. ........................................... 564/282; 562/8
(58) Field of Search ................................ 564/281, 282; 562/8

(56) References Cited

U.S. PATENT DOCUMENTS

| | | | |
|---|---|---|---|
| 3,050,521 A | * 8/1962 | Niederhauser | |
| 3,910,866 A | 10/1975 | Morris | 260/80.81 |
| 3,919,143 A | 11/1975 | Morris | 260/18 |
| 4,252,662 A | 2/1981 | Marolewski et al. | 252/78.5 |
| 4,521,412 A | 6/1985 | Schmitt et al. | 514/244 |
| 4,716,037 A | 12/1987 | Erdman et al. | 424/70 |
| 4,929,454 A | 5/1990 | Findlay et al. | 424/638 |
| 5,266,567 A | 11/1993 | Hsu | 514/212 |
| 5,290,805 A | 3/1994 | Eastman et al. | 514/642 |
| 5,300,635 A | 4/1994 | Macfarlane | 536/25.4 |
| 5,399,762 A | 3/1995 | Walker | 564/296 |
| 5,438,034 A | 8/1995 | Walker | 504/158 |
| 5,523,487 A | 6/1996 | Walker | 564/296 |
| 5,545,749 A | * 8/1996 | Smith et al. | |
| 5,559,155 A | 9/1996 | Walker | 514/642 |
| 5,561,187 A | 10/1996 | Bechara et al. | 524/591 |
| 5,567,372 A | 10/1996 | Nohr et al. | 264/103 |

FOREIGN PATENT DOCUMENTS

GB 1199015 7/1970

OTHER PUBLICATIONS

CA:119:219593 abs of JP05186208, Jan. 1992.*
CA: 103:17899 abs of J. Chromatogr. by Abidi 324(2) pp 209–230, 1985.*
CA:120:195236 abs of SU 1782935, Dec. 1992.*
Journal of American Wood Preservativer's Association (1987), pp. 331–348.

* cited by examiner

Primary Examiner—Jean F. Vollano
(74) Attorney, Agent, or Firm—Baker Botts L.L.P.

(57) ABSTRACT

Disclosed is quaternary ammonium phosphate compound having formula (1) and which has an anticorrosive and a biocidal efffect to have a capability of preventing corrosion of various metals including corrosive metal substances, e.g. carbon steels, iron casts, stain steels, coppers, tinning steel plates or alumina and an efficient method of preparing the same. In formula (1), $R_1$ is a straight or a branched alkyl or aryl radical with 1 to 27 carbon atom(s) free of —OH group and may contain hereto-atoms, and both $R_2$ and $R_3$ are methyl groups or $R_2$ and $R_3$ are combined to form a heterocyclic compound with 4 to 6 of carbon atoms containing oxygen and nitrogen.

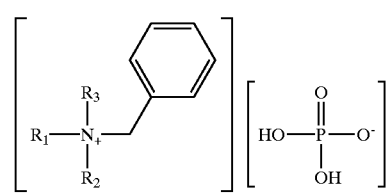

(1)

5 Claims, No Drawings

QUATERNARY AMMONIUM PHOSPHATE COMPOUND AND METHOD OF PREPARING SAME

CROSS REFERENCE TO RELATED APPLICATION

This application is the national phase of PCT/KR98/00099, now WO 99/12889.

This application is based on application No. 97-46517 filed in Korean Industrial Property Office on Sep. 10, 1997, the content of which is incorporated hereinto by reference.

BACKGROUND OF THE INVENTION (a) Field of the Invention

The present invention relates to a novel quaternary ammonium phosphate compound and, more particularly, to a quaternary ammonium phosphate compound having the following formula 1 and which has an anticorrosive and a biocidal effect and an efficient method of preparing the same.

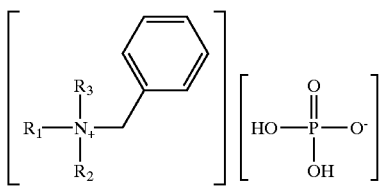

Formula 1

In the above formula 1, $R_1$ is a straight or a branched alkyl or aryl radical with 1 to 27 of carbon atom(s) free of —OH group and may contain hetero-atoms, and both of $R_2$ and $R_3$ are methyl groups or $R_2$ and $R_3$ are combined to form a heterocyclic compound with 4 to 6 of carbon atoms containing oxygen and nitrogen.

(b) Description of the Related Arts

A quaternary ammonium halide containing a quaternary ammonium salt as a parental core, particularly, a quaternary ammonium chloride has the advantages of having, a high biocidal effect and a low degree of surface tension and toxicity and hence, it is often used for the purpose of cleaning and sterilizing various household and industrial goods. And it is also widely used as an additive in wood preservatives, paints, industrial water-treating agents, cleansers and biocides because it is highly stable.

A quaternary ammonium halide is typically prepared by using the following reaction formula.

$R_1R_2R_3N+R_4X \rightarrow R_1R_2R_3R_4NX$     Reaction formula 1

In the above reaction formula 1, $R_1$, $R_2$, $R_3$ and $R_4$ are independently alkyl or aryl radicals and X is a halogen compound.

Recently, quaternary ammonium chlorides, particularly, N-alkyl-N-benzyl-N-dimethyl ammonium chloride and N-dialkyl-N-dimethyl ammonium chloride have been the subject of many studies. They are disclosed in U.S. Pat. Nos. 3,919,143 and 3,910,866 as polymer hardening promoters, disclosed in U.S. Pat. No. 5,300,635 as surfactants for separation of RNA and disclosed in U.S. Pat. Nos. 5,290,805, 5,399,762, 5,561,187 and 5,567,372 as common biocides. U.S. Pat. No. 4,929,454 and Journal of American Wood Preservativer's Association(1987) pages 331~348 by A. F. Preston disclose a technique for preserving wood by impregnating the quaternary ammonium chloride in the wood.

U.S. Pat. No. 4,521,412 discloses iodopropargylammonium salts having a pesticidal effect and a method of preparing the same, and U.S. Pat. No. 5,266,567 discloses halopropargylated cyclic quaternary ammonium compounds and a method of preparing the same.

But all the above-described compounds have a high biocidal effect in a water system, but as they release halogen compounds such as fluorine, chlorine, bromine and iodine, they are difficult to apply to corrosive metal substances such as carbon steels, cast irons, stain steels or coppers. Accordingly, U.S. Pat. No. 5,438,034 (1995) discloses a quaternary ammonium carbonate and a method of preparing the same, the quaternary ammonium carbonate having the following formula 5 and which has no metal coupler and which can be obtained easily to be used as a wood preservative. The method adopts directly a gaseous or solid carbon dioxide as a carbonic acid of a reactant.

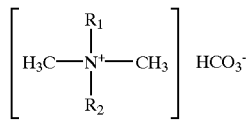

Formula 5

In the above formula 5, both $R_1$ and $R_2$ are alkyl groups with 8 to 12 of carbon atoms.

U.S. Pat. No. 5,399,762 (1995) discloses a quaternary ammonium hydroxide and a method of preparing the same, the quaternary ammonium hydroxide being used as a wood preservative. An aqueous solution containing 80% quaternary ammonium chloride is used as a starting material and the equilibrium of a reaction is shifted by raising a temperature to 40~90° C. so that the quaternary ammonium hydroxide can be prepared. However, if the temperature is raised as in the above, a parental core of the quaternary ammonium salt undergoes a Hofmann elimination and rearrangement reaction when the parental core is exposed under a high-temperature alkaline condition so that a yellowish-brown oily olefin and amine compounds emitting an amine ordor are formed. The compounds are highly hygroscopic and difficult to separate. In addition, in drying the ammonium hydroxide, a considerable quantity of the compound is decomposed.

Moreover, all the above-described compounds have been developed and designed only as common biocides and except for the quaternary ammonium hydroxide, they are limited to a structure that a leaving group of a reactant are ion-bonded with the quaternary ammonium salt as an anionic conjugate of the compound In another aspect, United Kingdom Patent No. 1,199,015 (1968) and U.S. Pat. No. 4,252,662 (1981) disclose a method of introducing a phosphoric ester as an anionic conjugate. However, this method adopts the phosphoric ester as a reactant and is applied in the field of a base material of a high-pressure fluid. And U.S. Pat. No. 4,716,037 discloses a quaternary ammonium compound having an alkyl group with a terminal alcoholic group and which is used in hair conditioners for the purpose of lessening corrosion of stain steels.

SUMMARY OF THE INVENTION

It is an object of the present invention to provide a quaternary ammonium phosphate compound having the following formula 1 and which has both a strong anticorrosive effect on a wide range of metals and biocidal effect to be used in corrosive metal substances such as carbon steels, iron casts, stain steels, coppers, tinning steel plates and alumina by substituting a dihydrogen phosphate ion ($H_2PO_4$,) for a Cl ion from a quaternary ammonium chloride, and a method of preparing the same.

Particularly, a novel quaternary ammonium phosphate compound having the following formula 1 is characterized in that it has an ether group including an unshared electron pair to improve an anticorrosive characteristic greatly and to be able to form a nonoxidative anticorrosive membrane.

A first aspect of the present invention provides a quaternary ammonium phosphate compound having the following formula 1.

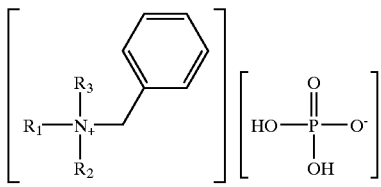

Formula 1

In the above formula, $R_1$ is a straight or a branched alkyl radical with 1 to 27 carbon atoms or aryl radical with 6 to 27 carbon atoms which does not contain —OH groups as substitutents on the carbon atoms, and may contain heteroatoms in the alkyl or aryl chain; and both of $R_2$ and $R_3$ are methyl groups or $R_2$ and $R_3$ are combined to form a heterocyclic compound with 4 to 6 carbon atoms containing oxygen and nitrogen.

$R_1$ is preferably p-($\alpha,\alpha,\gamma,\gamma$)-tetramethyl butyl phenoxy ethoxy ethyl group, and $R_2$ and $R_3$ are preferably methyl groups.

And $R_1$ is preferably a tetradecyl group, and $R_2$ and $R_3$ are preferably morpholinium groups having the following formula 2.

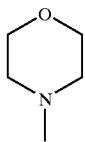

Formula 2

The second aspect of the present invention provides a method of preparing a quaternary ammonium phosphate compound having the above formula 1 having the step of reacting a quaternary ammonium hydroxide having the following formula 3 with a phosphoric acid.

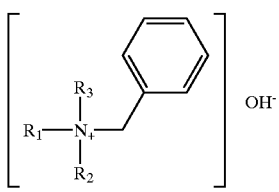

Formula 3

In the above formula 3, $R_1$, $R_2$ and $R_3$ are the same as defined above.

The quaternary ammonium hydroxide is preferably prepared by reacting a solid quaternary ammonium chloride having the following formula 4 with a metal hydroxide of 1.05~2.0 equivalents to the quaternary ammonium chloride in a solvent containing an alcohol with 1 to 4 of carbon atom(s) at 0~35° C.

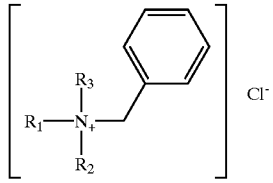

Formula 4

In the above formula 4, $R_1$, $R_2$ and $R_3$ are the same as defined above.

The third aspect of the present invention provides a composition having an anticorrosive and a biocidal effect, containing a quaternary ammonium phosphate compound having the above formula 1.

DETAILED DESCRIPTION OF THE PREFERRED EMBODIMENTS

A quaternary ammonium phosphate compound having the above formula 1 is prepared as follows.

Reaction formula 2

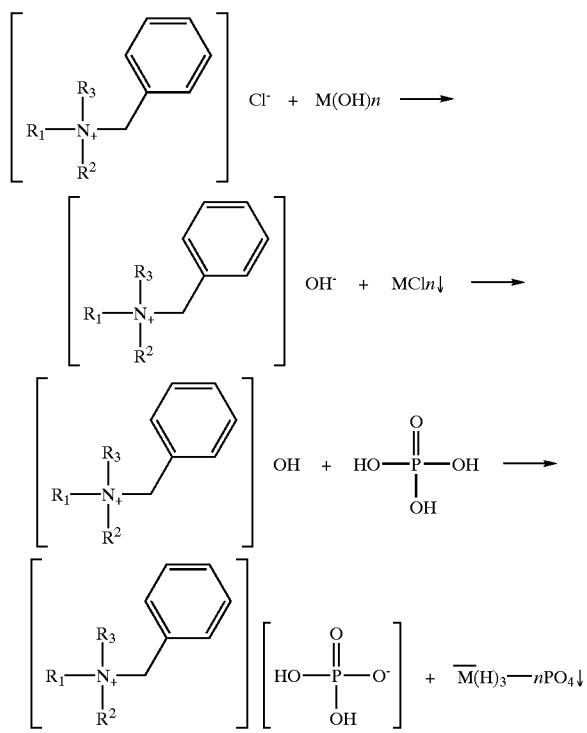

A quaternary ammonium chloride contains a N-benzyl group in a parental core of a quaternary ammonium salt and is preferably selected from the group consisting of N-dimethyl-N-[p-(($\alpha,\alpha,\gamma,\gamma$)-tetramethyl butyl phenoxy] ethoxy ethyl-N-benzyl ammonium chloride, a mixture of N-dimethyl-N-dodecyl-N-benzyl ammonium chloride, N-dimethyl-N-tetradecyl-N-benzyl ammonium chloride, N-dimethyl-N-hexadecyl-N-benzyl ammonium chloride and N-dimethyl-N-octadecyl-N-benzyl ammonium chloride, and 4-benzyl-4-tetradecyl morpholinium, chloride. The metal hydroxide contains a mono-, di- or trivalent metal, preferably a monovalent metal, and more preferably sodium or potassium.

A step for preparing the quaternary ammonium hydroxide is a typical equilibrium reaction so that the reaction can be optimized by changing the ratio of equivalents of reactants, solvents and conditions of the reaction. The step is preferably carried out in a solvent containing an alcohol with 1 to 4 of carbon atom(s), preferably an ethanol, and more preferably an anhydrous ethanol. When a mixture of N-dimethyl-N-dodecyl-N-benzyl ammonium chloride, N-dimethyl-N-tetradecyl-N-benzyl ammonium chloride, N-dimethyl-N-hexadecyl-N-benzyl ammonium chloride and N-dimethyl-N-octadecyl-N-benzyl ammonium chloride is used as a starting material, the content of water can be minimized and the yield can be maximized by using the solid mixture having been crystallized with a drying method such as a lyophilization method. The metal hydroxide is preferably 1.05~2.0 equivalents to the quaternary ammonium chloride. If less 1.05 equivalents, the reaction rate is decreased and if more 2.0 equivalents, decomposition reaction may occur. The reaction is performed at 0~35° C. so that a Hofmann elimination and rearrangement reaction occurring under a high-temperature alkaline condition can be suppressed and the reaction can be finished within 8 hours. Therefore, a filtrate containing the quaternary ammonium hydroxide is not required to separate and can be used directly in the subsequent step so that the prior filtrate drying step, where a considerable quantity of the quaternary ammonium hydroxide is decomposed, can be omitted.

A reaction between a quaternary ammonium hydroxide and a phosphoric acid is a neutralization reaction and even if some heat is generated, another side reaction is not likely to occur and therefore a separate cooling step is not required. If the residual metal hydroxide remains in the solution, it reacts quickly with dihydrogen phosphate ions preferentially and can be extracted and removed easily in the form of a metal phosphate salt.

A quaternary ammonium chloride having the above formula 4 is added and dissolved at room temperature in an alcohol solvent with 1 to 4 of carbon atom(s). A small quantity of a metal hydroxide containing a mono-, di- or trivalent metal is admixed and the solution is agitated for 1~8 hour(s). As the reaction is proceeded, a metal chloride is precipitated and the solution becomes turbid. After the reaction ends, the solution is cooled at a low temperature of about 0° C. and a white metal chloride is completely removed. Then a filtrate containing a quaternary ammonium hydroxide intermediate having the above formula 3 is obtained. A phosphoric acid of equivalents corresponding to those of the quaternary ammonium hydroxide intermediate and the residual metal hydroxide is added with a dropping funnel at room temperature and an acid-base reaction is proceeded. A metal phosphate is extracted and separated with a filter. Removal of the solvent from the obtained solution by drying gives an oily paste or a white powdery quaternary ammonium phosphate.

A preferred embodiment of this invention will be explained with reference to the following examples.

EXAMPLES

Example 1

Preparation of solid- N-dimethyl-N-[p-($\alpha,\alpha,\gamma,\gamma$)-tetramethyl butyl phenoxy]ethoxy ethyl-N-benzyl ammonium phosphate 50 ml of ethanol was added in a 100 ml round flask. 10.0 g (22 mmol) of N-dimethyl-N-[p-($\alpha,\alpha,\gamma,\gamma$)-tetramethyl butyl phenoxy]ethoxy ethyl-N-benzyl ammonium chloride was added and dissolved at room temperature and then 2.21 g (33 mmol, 85%) of ground potassium hydroxide was added. Equipped with an anhydrous calcium chloride tube, the solution was agitated at a high rate for 6 hours. Precipitates were formed in the solution after the elapse of time. The solution was cooled in an ice bath and filtered off. Washing of the precipitates with cold ethanol gave 1.6 g of potassium chloride. 4.18 g (33 mmol) of 85% phosphoric acid was admixed with the filtrate and after 1 hour, the residual potassium phosphate was extracted and filtered. Removal of the solvent and drying of the solid gave 11.0 g of solid N-dimethyl-N-[p-(($\alpha,\alpha,\gamma,\gamma$)-tetramethyl butyl phenoxy] ethoxy ethyl-N-benzyl ammonium phosphate.

A result of a $^1$H-NMR analysis of the compound is shown as $\delta$ 7.60~7.40(m,5H), 7.26~7.27(d,2H), 6.78(d.2H), 4.93 (s,2H), 4.12~3.90(t,8H), 3.30(s,6H), 1.69(s,6H), 1,69(s,6H), 1.33(s,6H) and 0.70(s,9H).

Example 2

Preparation of powdery N-dimethyl-N-[p-($\alpha,\alpha,\gamma,\gamma$)-tetramethyl butyl phenoxy]ethoxy ethyl-N-benzyl ammonium phosphate 9.68 g of solid N-dimethyl-N-[p-($\alpha,\alpha,\gamma,\gamma$)-tetramethyl butyl phenoxy]ethoxy ethyl-N-benzyl ammonium phosphate obtained in example 1 was dissolved in 4 ml of boiling isopropyl alcohol and recrystallized with a boiling ethylacetate solvent. 7.50 g of white powdery N-dimethyl-N-[p-($\alpha,\alpha,\gamma,\gamma$)-tetramethyl butyl phenoxy]ethoxy ethyl-N-benzyl ammonium phosphate was obtained.

The melting point of the compound was 188~192° C. and a result of a $^1$H-NMR analysis of the compound is shown as $\delta$ 7.60~7.40(m,5H), 7.26~7.27(d,2H), 6.78(d.2H), 4.93(s, 2H), 4.12(t,4H), 4.05(t,2H), 3.30(s,6H), 1.69(s,2H), 1.33(s, 6H) and 0.70(s,9H).

Example 3

Preparation of a mixture of N-dimethyl-N-dodecyl-N-benzyl ammonium phosphate, N-dimethyl-N-tetradecyl-N-benzyl ammonium phosphate, N-dimethyl-N-hexadecyl-N-benzyl ammonium phosphate and N-dimethyl-N-octadecayl-N-benzyl ammonium phosphate 1.2 l of ethanol was added in a 2 l two-mouthed round flask. A mixture of N-dimethyl-N-dodecyl-N-benzyl ammonium chloride, N-dimethyl-N-tetradecyl-N-benzyl ammonium chloride, N-dimethyl-N-hexadecyl-N-benzyl ammonium phosphate and N-dimethyl-N-octadecyl-N-benzyl ammonium chloride was dried in a lyophilizer of −50° C. and 5 torr. 360 g (1.02 mol) of the mixture was added and dissolved at room temperature. 93.45 g (1.42 mol) of 85% ground potassium hydroxide was added. Equipped with an anhydrous calcium chloride tube, the solution was agitated at a high rate for 8 hours. Precipitates were formed in the solution after the elapse of time. The solution was cooled in an ice bath and filtered off. Washing of the precipitates with cold ethanol gave 75 g of potassium chloride. 163.26 g (1.42 mol) of 85% phosphoric acid was admixed with the filtrate and after 1 hour, the residual potassium phosphate was extracted and filtered off. Removal of the solvent and admixing of an ethyl acetate solvent gave a uniform slurry. Separation and drying of the slurry gave 390 g of the mixture of N-dimethyl-N-dodecyl-N-benzyl ammonium phosphate, N-dimethyl-N-tetradecyl-N-benzyl ammonium phosphate, N-dimethyl-N-hexadecyl-N-benzyl ammonium phosphate and N-dimethyl-N-octadecayl-N-benzyl ammonium phosphate.

A result of a ¹H-NMR analysis of the compound is shown as δ 7.48~7.44(m,5H), 4.52(s,2H), 3.11 (s,6H), 3.05(t,2H) and 0.87(t,3H).

Example 4

Preparation of 4-benzyl-4-tetradecyl morpholinium ammonium phosphate.

5 ml of ethanol was added in a 50 ml round flask. 4.26 g (10 mmol) of 4-benzyl-4-tetradecyl morpholinium ammonium chloride was added and dissolved at room temperature. 420 mg (10.5 mmol) of ground potassium hydroxide was added. Equipped with an anhydrous calcium chloride tube, the solution was agitated at a high rate for 8 hours. Precipitates were formed in the solution with the elapse of time. The solution was cooled in an ice bath and filtered off. Washing of the precipitates with cold ethanol gave 550 mg of sodium chloride. 1.21 g (10.5 mmol) of 85% phosphoric acid was admixed with the filtrate and after 1 hour, the residual potassium phosphate was extracted and filtered off. Removal of the solvent and admixing of 20 ml of an ethyl acetate solvent gave a uniform slurry. Drying of the slurry gave 4.15 g of yellowish-brown solid 4-benzyl-4-tetradecyl morpholinium ammonium phosphate A result of a ¹H-NMR analysis of the compound is shown as δ 7.53(m,5H), 4.68(s,2H), 4.10(t, 4H), 4.00(t,2H), 3.39(t, 4H), 1.37~1.29(m,22H), 1.38(m,2H) and 0.88(t,3H).

Comparative example 1

Preparation of N-dimethyl-N-[p-N-[p-((α,α,γ,γ)-tetramethyl butyl phenoxy]ethoxy ethyl-N-benzyl ammonium phosphate.

Example 1 was repeated except that the solution was agitated for 30 minutes at room temperature and that after the reaction with the phosphoric acid, the solvent was removed and an ethyl acetate solvent was added to obtain a uniform slurry. Filtration and drying of the slurry gave N-dimethyl-N-[p-N-[p-(α,α,γ,γ)-tetramethyl butyl phenoxy]ethoxy ethyl-N-benzyl ammonium phosphate.

Comparative example 2

Preparation of 4-benzyl-4-tetradecyl morpholinium ammonium phosphate.

Example 4 was repeated except that the reaction was carried out in an ice bath containing a saturated sodium chloride solution. 310 mg of potassium chloride was formed as an intermediate and 4-benzyl-4-tetradecyl morpholinium ammonium phosphate was finally obtained.

Comparative example 3

Preparation of a mixture of N-dimethyl-N-dodecyl-N-benzyl ammonium phosphate, N-dimethyl-N-tetradecyl-N-benzyl ammonium phosphate, N-dimethyl-N-hexadecyl-N-benzyl ammonium phosphate and N-dimethyl-N-octadecayl-N-benzyl ammonium phosphate Example 3 was repeated except that the quaternary ammonium chlorides were not lyophilized and used in the form of a 50% aqueous solution. A mixture of N-dimethyl-N-dodecyl-N-benzyl ammonium phosphate, N-dimethyl-N-tetradecyl-N-benzyl ammonium phosphate, N-dimethyl-N-hexadecyl-N-benzyl ammonium phosphate and N-dimethyl-N-octadecayl-N-benzyl ammonium phosphate was obtained.

The yields of the examples and the comparative examples are shown below in table 1.

TABLE 1

| | Yield(%) |
|---|---|
| Example 1 | 99 |
| Example 2 | 77.5 |
| Example 3 | 93.8 |
| Example 4 | 88 |
| Comparative example 1 | 68 |
| Comparative example 2 | 49 |
| Comparative example 3 | 45 |

As shown in table 1, the preparation method of the present invention easily obtains a quaternary ammonium phosphate in a high yield.

Anticorrosive Effect Test

This test was carried out for the purpose of measuring an anticorrosive effect of the compounds obtained from examples 1, 3 and 4. An anhydrous calcium chloride and magnesium sulfate 7 hydrates were mixed in 1 l of pure water to formulate 15 ppm of magnesium hardness. A test material was added to 20 ppm and the final pH was adjusted to 8.5. A water tank at 40° C. was used, 100 cc of air was supplied per minute and the solution was agitated at 150 rpm. A metal test piece used were carbon steel (c-1020), copper, cast iron, tinning steel plate of which the surface areas were respectively 0.21 g/dm², 0.20 g/dm², 0.22 g/dm², and 0.17 g/dm². The rate of corrosion was analyzed from the weight loss of the test piece after 42 hours and the measuring unit was mpy(mils per year).

Biocidal Effect Test

This test was carried out for the purpose of measuring a biocidal effect of the compounds obtained from examples 1, 3 and 4. A test material was diluted using a serial dilution method in a 96-multiwelled plate. 10⁴ cfu/ml of microbes were inoculated in the diluted solution. After the microbes were cultivated for 48 hours at 30° C., MIC (Minimal Inhibition Concentration of microorganisms) was visually observed to decide whether or not microbial growth occurred from the turbidity. The growth medium was nutrient broth, DIFCO, and the strains used were as follows.

Bacteria

Enterobacter aerogenes ATCC 13048, *Escherichia coli* ATCC 11229, *Micrococcus luteus* ATCC 9431, *Pseudomonas aeruginosa* ATCC 15442, *Shigella sonnei* ATCC 9290, *Staphylococcus epidermis* ATCC 155, *Staphylococcus aureus* ATCC 6538 and *Bacillus subtilis* ATCC 6984.

Yeasts

*Candida albicans* ATCC 10231, *Rhodotorula rubra* ATCC 9449, *Cryptococcus neoformans* ATCC 34144 and *Saccharomyces cerevisiae* ATCC 9763.

Fungi

*Penicillium citrinum* ATCC 98404, *Trichoderma viridae* ATCC 1287, *Rhizopus oryzae* ATCC 10404 and *Aspergillus niger* ATCC 9642.

Test results are shown below in table 2.

TABLE 2

| | Anticorrosive effect (mpy) | | | | Minimal Inhibition Concentration (ppm) | | |
|---|---|---|---|---|---|---|---|
| | carbon steel | cast iron | copper | tinning steel | Bacteria | yeasts | fungi |
| example 1 | 4.5 | 1.3 | 0.1 | 0.1 | 6.3~12.5 | 6.3~12.5 | 25~100 |
| example 3 | 3.7 | 4.6 | 0.2 | 0.3 | 12.5~25 | 12.5~25 | 25~100 |
| example 4 | 5.1 | 0.8 | 0.1 | 0.1 | 6.3~12.5 | 12.5~25 | 25~100 |
| A | 7.2 | 6.5 | 0.5 | 0.5 | 12.5~25 | 12.5~25 | 25~100 |
| B | 6.8 | 7.1 | 0.4 | 0.7 | 6.3~12.5 | 6.3~25 | 25~100 |
| C | 10.5 | 11.1 | 0.3 | 0.6 | 6.3~12.5 | 12.5~50 | 25~100 |
| D | 18.7 | 13.9 | 0.1 | 0.3 | — | — | — |
| E | 7.6 | 5.1 | 0.2 | 0.3 | — | — | — |
| F | 33.0 | 25.5 | 0.7 | 1.9 | — | — | — |

A: N-dimethyl-N-[p-(α,α,γ,γ)-tetramethyl butyl phenoxy]ethoxy ethyl-N-benzyl chloride
B: 4-benzyl-4-tetradecyl morpholinium ammonium chloride
C: a mixture of N-dimethyl-N-dodecyl-N-benzyl ammonium chloride, N-dimethyl-N-tetradecyl-N-benzyl ammonium chloride, N-dimethyl-N-hexadecyl-N-benzyl ammonium chloride and N-dimethyl-N-octadecyl-N-benzyl ammonium chloride
D: sodium dihydrogen phosphate (NaH$_2$PO$_4$.12H$_2$O)
E: N-dimethyl-N-cetyl-N-hydroxyethyl ammonium phosphate
F: Blank (no compound contained)

As shown in table 2, the quaternary ammonium phosphate compounds of the present invention have a high anticorrosive effect on carbon steels, cast irons, coppers and tinning steel plates. This results from a synergic effect between an ether bond of an unshared electron pair in an alkyl group of a parental core of, a quaternary ammonium and phosphate of an anion. The compound also has a high anticorrosive effect.

The present invention provides a compound which has an anticorrosive effect on a wide range of corrosive metal substances e.g. carbon steels, iron casts, stain steels, coppers., tinning steel plates and alumina and which has a biocidal effect, a cleaning effect and a low toxicity. The compound is useful where a strong biocidal effect is required, where a cleaning effect is required and where low toxicity and where low skin irritability is required and when applied to equipment, devices or apparatus made of corrosive substances. Moreover, the compound has properties to allow performance of a substitution reaction, and provides high purity and low toxicity so that it can be easily used on a commercial scale.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A quaternary ammonium phosphate compound having an anticorrosive and a biocidal effect, the compound having the formula

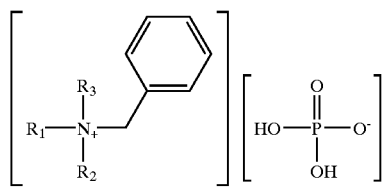

wherein R$_1$ is a p-(α,α,γ,γ)-tetramethyl butyl phenoxy ethoxy ethyl group, and R$_2$ and R$_3$ are methyl groups.

2. A quaternary ammonium phosphate compound having an anticorrosive and a biocidal effect, the compound having the formula

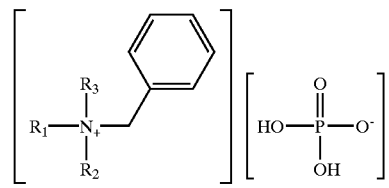

wherein R$_1$ is a tetradecyl group, and R$_2$ and R$_3$ together form a morpholinium group having the following formula

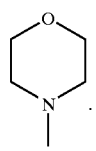

3. A method of preparing a quaternary ammonium phosphate compound having the formula

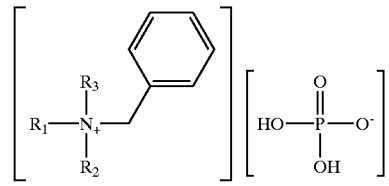

wherein R$_1$ is a straight or branched alkyl radical with 1 to 27 carbon atoms or aryl radical with 6 to 27 carbon atoms, which does not contain —OH groups as substitutents on the carbon atoms, and may contain heteroatoms in the alkyl or aryl chain; and both of R$_2$ and R$_3$ are methyl groups or R$_2$ and R$_3$ together form a morpholinium group having the following formula,

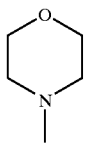

the method comprising the steps of:
(a) reacting a quaternary ammonium chloride having the following formula

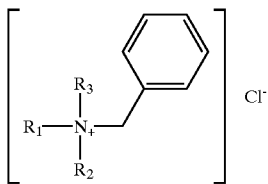

with 1.05 to 2.0 equivalents of metal hydroxide per equivalent of the quaternary ammonium chloride in a solvent containing an alcohol with 1 to 4 carbon atom(s) at 0 to 35° C., wherein $R_1$, $R_2$, and $R_3$ are the same as defined above, to obtain a quaternary ammonium hydroxide having the following formula

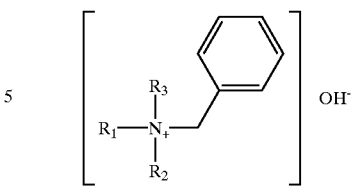

wherein $R_1$, $R_2$ and $R_3$ are the same as defined above; and (b) reacting the quaternary ammonium hydroxide with phosphoric acid at a temperature between about 0° C. and about 19° C. to obtain the quaternary ammonium phosphate compound.

4. A composition having an anticorrosive and a biocidal effect comprising:

the quaternary ammonium phosphate compound of claim 1.

5. A composition having an anticorrosive and a biocidal effect comprising:

the quaternary ammonium phosphate compound of claim 2.

* * * * *